United States Patent
Honda et al.

(10) Patent No.: US 10,287,391 B2
(45) Date of Patent: May 14, 2019

(54) POLYESTER RESIN AND PRODUCTION METHOD THEREFOR

(71) Applicant: MITSUBISHI GAS CHEMICAL COMPANY, INC., Tokyo (JP)

(72) Inventors: Eiichi Honda, Kanagawa (JP); Yasuaki Yoshimura, Kanagawa (JP); Yuichiro Satake, Kanagawa (JP); Takashi Motoi, Okayama (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/575,150

(22) PCT Filed: May 24, 2016

(86) PCT No.: PCT/JP2016/065337
§ 371 (c)(1),
(2) Date: Nov. 17, 2017

(87) PCT Pub. No.: WO2016/190317
PCT Pub. Date: Dec. 1, 2016

(65) Prior Publication Data
US 2018/0142059 A1    May 24, 2018

(30) Foreign Application Priority Data

May 27, 2015    (JP) .................................. 2015-107183
Mar. 25, 2016    (JP) .................................. 2016-061737

(51) Int. Cl.
*C08G 63/02*    (2006.01)
*C08G 63/06*    (2006.01)
*C07C 69/757*    (2006.01)
*C08G 63/78*    (2006.01)

(52) U.S. Cl.
CPC ............ *C08G 63/06* (2013.01); *C07C 69/757* (2013.01); *C08G 63/78* (2013.01); *C07C 2603/86* (2017.05)

(58) Field of Classification Search
USPC ......... 524/423, 424, 427, 437; 528/271, 272
See application file for complete search history.

(56) References Cited

U.S. PATENT DOCUMENTS

| | | |
|---|---|---|
| 2005/0124779 A1 | 6/2005 | Shelby et al. |
| 2012/0203026 A1 | 8/2012 | Kawakami et al. |
| 2017/0088504 A1 | 3/2017 | Motoi et al. |

FOREIGN PATENT DOCUMENTS

| | | |
|---|---|---|
| EP | 3275856 A | 1/2018 |
| JP | S58-174419 A | 10/1983 |
| JP | S61015096 B2 | 4/1986 |
| JP | 2000281613 A | 10/2000 |
| JP | 2001-064372 A | 3/2001 |
| JP | 2001-064374 A | 3/2001 |
| JP | 2003-119259 A | 4/2003 |
| JP | 2007-161917 A | 6/2007 |
| JP | 2007-517926 A | 7/2007 |
| JP | 2008-133223 A | 6/2008 |
| WO | 201148851 A1 | 4/2011 |
| WO | 2012035874 A1 | 3/2012 |
| WO | 2015147242 A1 | 10/2015 |

OTHER PUBLICATIONS

International Search Report from Patent Application No. PCT/JP2016/065337, dated Jun. 21, 2016.
T. Sugimoto et al., Syn Selectivity in Diels-Alder Reactions of Isodicyclopentadiene, J. Org. Chem., 1976, vol. 41, No. 8, pp. 1457-1459.
Toru Kikuchi et al., "Stereostructure and Composition of Products from Hydroformylation of Dicyclopentadiene using Carbon Dioxide as a Reactant", Hitachi Kasei Technical Report, 2008, No. 51, pp. 7-12.
International Preliminary Report on Patentability from Patent Application No. PCT/JP2016/065337 dated Nov. 28, 2017.

*Primary Examiner* — Terressa Boykin
(74) *Attorney, Agent, or Firm* — Greenblum & Bernstein, P.L.C.

(57) ABSTRACT

A polyester resin according to the present invention comprises a constitutional unit represented by general formula (1):

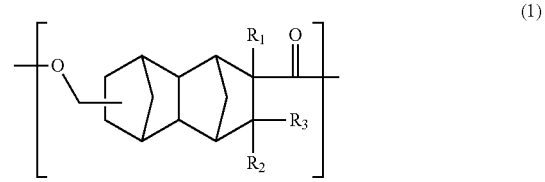

(1)

wherein $R_1$ is a hydrogen atom, $CH_3$, or $C_2H_5$; and $R_2$ and $R_3$ are each independently a hydrogen atom or $CH_3$.

2 Claims, 2 Drawing Sheets

POLYESTER RESIN AND PRODUCTION METHOD THEREFOR

TECHNICAL FIELD

The present invention relates to a polyester resin and a production method therefor.

BACKGROUND ART

Polyethylene terephthalate (hereinafter sometimes referred to as "PET") is a polyester resin that is characterized by excellent transparency, mechanical strength, melt stability, solvent resistance, aroma retaining properties, and recyclability, and is widely utilized in film, sheet, hollow containers, and the like. However, it cannot be said that PET has a sufficiently high glass transition temperature, also transparency may be impaired due to its crystallinity when a thick molded article is obtained, and therefore modification by copolymerization is widely carried out.

For example, polyester resins are proposed in which 1,4-cyclohexanedimethanol, tricyclodecanedimethanol, or pentacyclopentadecanedimethanol is used as a copolymerization component for polyesters. Since tricyclodecanedimethanol and pentacyclopentadecanedimethanol have a bulky, rigid skeleton, polyester resins involving these have a high glass transition temperature, the crystallinity is suppressed, and it is thus possible to increase the transparency of a molded article (see, for example, Patent Literatures 1 and 2).

On the other hand, among the aliphatic polyesters in which completely no aromatic components are used, polyesters with an alicyclic structure have excellent transparency and water resistance, and thus a large number of methods involving an alicyclic monomer represented by 1,4-cyclohexanedimethanol are proposed. For example, Patent Literature 3 discloses an aliphatic polyester composed of 1,4-cyclohexanedimethanol with 1,4-cyclohexanedicarboxylic acid or the like. Also, for increased heat resistance of aliphatic polyesters, polyesters having a norbornane skeleton are proposed (see, for example, Patent Literatures 4 and 5).

CITATION LIST

Patent Literature

Patent Literature 1: Japanese Patent Application No. 58-174419
Patent Literature 2: Japanese Patent Laid-Open No. 2003-119259
Patent Literature 3: Japanese Patent Laid-Open No. 2007-517926
Patent Literature 4: Japanese Patent Laid-Open No. 2001-64372
Patent Literature 5: Japanese Patent Laid-Open No. 2001-64374

SUMMARY OF INVENTION

Technical Problem

The polyester resins described in Patent Literatures 1 and 2 are inferior in not only UV resistance but also light transmittance and the like because the dicarboxylic acid component is aromatic. The transparency of the aliphatic polyester of Patent Literature 3 is good, but the heat resistance is not very high. Although the polyester resins having a norbornane skeleton disclosed in Patent Literatures 4 and 5 exhibit better heat resistance than polyester resins in which 1,4-cyclohexanedimethanol and 1,4-cyclohexanedicarboxylic acid are used as monomers, further improvements are required.

The present invention has been conceived in view of the problems of the conventional art above, and an object of the present invention is to provide a polyester resin having excellent heat resistance and transparency.

Solution to Problem

As a result of having conducted diligent research to solve the above problems, the inventors found that the above problems can be solved by providing a constitutional unit having a specific alicyclic structure in the main skeleton.

That is, the present invention is as follows.

<1>
A polyester resin comprising a constitutional unit represented by general formula (1):

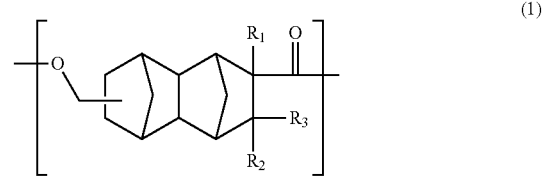

wherein $R_1$ is a hydrogen atom, $CH_3$, or $C_2H_5$; and $R_2$ and $R_3$ are each independently a hydrogen atom or $CH_3$.

<2>
A method for producing a polyester resin, comprising the step of polymerizing a compound represented by general formula (2):

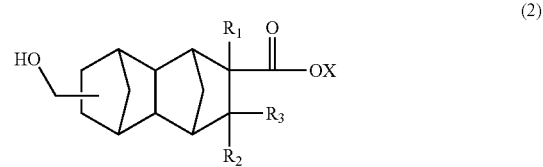

wherein $R_1$ is a hydrogen atom, $CH_3$, or $C_2H_5$; $R_2$ and $R_3$ are each independently a hydrogen atom or $CH_3$; and X is a hydrogen atom or a hydrocarbon group which has not more than 4 carbon atoms and which optionally comprises a hydroxyl group.

Advantageous Effect of Invention

The polyester resin of the present invention has excellent heat resistance and transparency.

DESCRIPTION OF EMBODIMENTS

Figure 1:
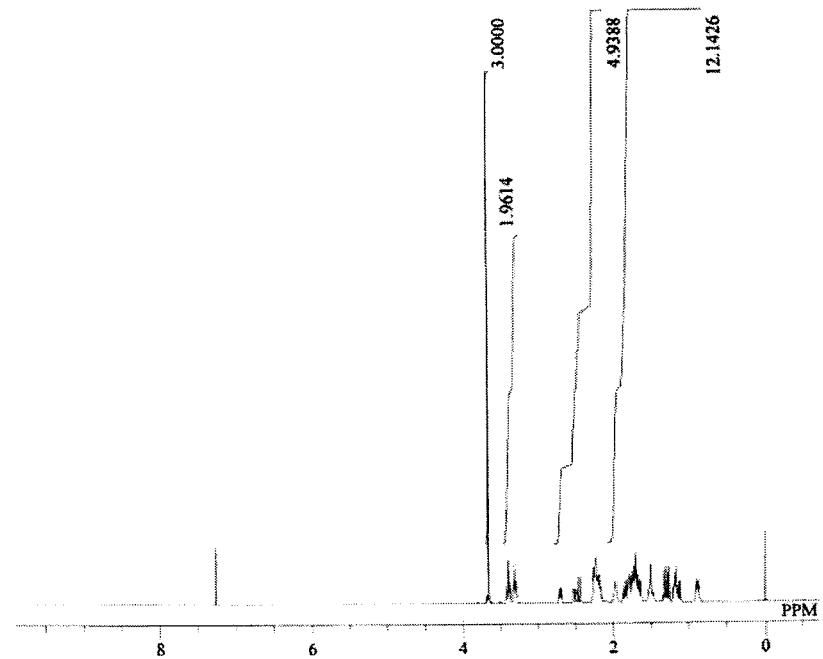
FIG. 1 shows the results of 1H-NMR measurement of the main reaction product obtained in the monomer synthesis example.

Below, an embodiment for carrying out the present invention (hereinafter simply referred to as "the present embodiment") will now be described in detail. The following present embodiment is an example for describing the present invention and is not intended to limit the present invention to the following contents. The present invention can be carried out after suitably making modifications within the scope of the present invention.

(A) Polyester Resin

The polyester resin of the present embodiment contains a constitutional unit represented by the following general formula (1) (hereinafter referred to as "constitutional unit (1)"):

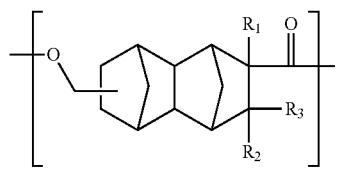

(1)

In constitutional unit (1), $R_1$ is a hydrogen atom, $CH_3$, or $C_2H_5$; and $R_2$ and $R_3$ are each independently a hydrogen atom or $CH_3$.

Being configured as above, the polyester resin of the present embodiment has excellent heat resistance and transparency. Having excellent heat resistance (a high glass transition temperature), transparency, and the like, the polyester resin of the present embodiment is suitable as optical materials, electronic parts, and medical materials.

$R_1$ is preferably a hydrogen atom or $CH_3$, and $R_2$ and $R_3$ are preferably hydrogen atoms.

The polyester resin of the present embodiment may contain a further constitutional unit other than constitutional unit (1) as long as the performance is not impaired.

The further constitutional unit is not particularly limited, and examples thereof include constitutional units derived from aromatic dicarboxylic acids such as terephthalic acid, isophthalic acid, phthalic acid, 1,3-naphthalenedicarboxylic acid, 1,4-naphthalenedicarboxylic acid, 1,5-naphthalenedicarboxylic acid, 2,6-naphthalenedicarboxylic acid, 2,7-naphthalenedicarboxylic acid, 2-methylterephthalic acid, biphenyldicarboxylic acid, and tetralindicarboxylic acid, and/or derivatives thereof; constitutional units derived from aliphatic dicarboxylic acids such as succinic acid, glutaric acid, adipic acid, pimelic acid, suberic acid, azelaic acid, sebacic acid, decanedicarboxylic acid, dodecanedicarboxylic acid, cyclohexanedicarboxylic acid, decalindicarboxylic acid, norbornanedicarboxylic acid, tricyclodecanedicarboxylic acid, pentacyclododecanedicarboxylic acid, 3,9-bis (1,1-dimethyl-2-carboxyethyl)-2,4,8,10-tetraoxaspiro[5.5] undecane, 5-carboxy-5-ethyl-2-(1,1-dimethyl-2-carboxyethyl)-1,3-dioxane, and dimer acid, and/or derivatives thereof; constitutional units derived from diols such as ethylene glycol, trimethylene glycol, 1,4-butanediol, 1,5-pentanediol, 1,6-hexanediol, diethylene glycol, propylene glycol, neopentyl glycol, 1,3-cyclohexanedimethanol, 1,4-cyclohexanedimethanol, 1,2-decahydronaphthalenedimethanol, 1,3-decahydronaphthalenedimethanol, 1,4-decahydronaphthalenedimethanol, 1,5-decahydronaphthalenedimethanol, 1,6-decahydronaphthalenedimethanol, 2,7-decahydronaphthalenedimethanol, tetralindimethanol, norbornanediol, xylylene glycol, 3,9-bis(1,1-dimethyl-2-hydroxyethyl)-2,4,8,10-tetraoxaspiro[5.5]undecane, 1,4:3,6-dianhydro-D-sorbitol, and 2,2,4,4-tetramethyl-1,3-cyclobutanediol; and constitutional units derived from oxyacids such as glycolic acid, lactic acid, hydroxybutyric acid, 2-hydroxyisobutyric acid, and hydroxybenzoic acid, and/or derivatives thereof. From heat resistance and transparency viewpoints, a constitutional unit having an aromatic ring or alicyclic structure is preferable.

The molecular weight of the polyester resin of the present embodiment can be suitably set in consideration of the desired performance, handleability, and the like, and is not particularly limited. The weight average molecular weight (Mw) in terms of polystyrene is preferably 5000 to 300,000, and more preferably 10,000 to 250,000. When Mw is 5,000 or more, there is a tendency that better heat resistance can be ensured, and when Mw is 300,000 or less, an excessive increase of melt viscosity is prevented, and removal of resin after production tends to be easy, and, furthermore, good flowability can be ensured, and therefore injection molding in a molten state tends to be easy.

The limiting viscosity (the measured value at 25° C. using a mixed solvent of phenol and 1,1,2,2-tetrachloroethane in a mass ratio of 6:4) of the polyester resin of the present embodiment is not particularly limited. From the viewpoint of the moldability of the polyester resin of the present embodiment, it is preferably 0.1 to 2.0 dL/g, and more preferably 0.2 to 1.5 dL/g. When the intrinsic viscosity is 0.1 dL/g or more, there is a tendency that sufficient mechanical strength can be ensured when the polyester resin of the present embodiment as a raw material is melt-molded into a molded article such as film, and when 1.5 dL/g or less, good flowability and moldability during melting can be ensured, and a molded article having excellent dimensional stability tends to be obtained.

Furthermore, when the polyester resin of the present embodiment is used, an antioxidant, a mold releasing agent, a UV absorber, a flowability modifier, a crystal nucleating agent, a reinforcement, a dye, an antistatic agent, an antibacterial agent, or the like is suitably added.

(B) Method for Producing Compound Represented by General Formula (2)

The polyester resin of the present embodiment is obtained by, for example, polymerizing a compound represented by the following general formula (2):

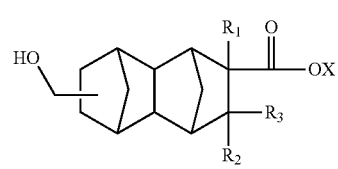

(2)

In the above general formula (2), $R_1$ is a hydrogen atom; $CH_3$, or $C_2H_5$; $R_2$ and $R_3$ are each independently a hydrogen atom or $CH_3$; and X is a hydrogen atom or a hydrocarbon group which has not more than 4 carbon atoms and which optionally comprises a hydroxyl group.

In formula (2), $R_1$ is preferably a hydrogen atom or $CH_3$. $R_2$ and $R_3$ are preferably hydrogen atoms. Examples of the above hydrocarbon group include, but are not limited to, a methyl group, an ethyl group, a propyl group, a butyl group, a vinyl group, a 2-hydroxyethyl group, and a 4-hydroxybutyl group.

The compound represented by general formula (2) in the present embodiment can be synthesized through, for example, the route shown in formula (I) using dicyclopentadiene or cyclopentadiene and an olefin having a functional group as raw materials:

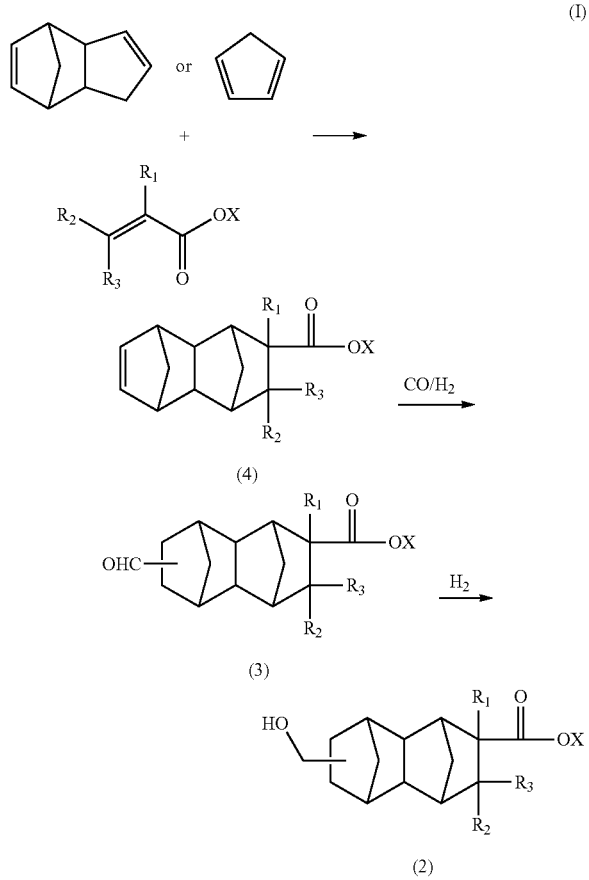

In formula (I), $R_1$ is a hydrogen atom, $CH_3$, or $C_2H_5$; $R_2$ and $R_3$ are each independently a hydrogen atom or $CH_3$; and X is a hydrogen atom or a hydrocarbon group which has not more than 4 carbon atoms and which optionally comprises a hydroxyl group.

[Production of Monoolefin Having 13 to 21 Carbon Atoms Represented by General Formula (4) in Formula. I)]

The monoolefin having 13 to 21 carbon atoms represented by general formula (4) in the present embodiment can be produced by, for example, carrying out a Diels Alder reaction of an olefin having a functional group with dicyclopentadiene.

Specific examples of the olefin having a functional group used in the Diels Alder reaction include, but are not limited to, methacrylic acid, methyl methacrylate, ethyl methacrylate, propyl methacrylate, butyl methacrylate, vinyl methacrylate, 2-hydroxyethyl methacrylate, 4-hydroxybutyl methacrylate, acrylic acid, methyl acrylate, ethyl acrylate, propyl acrylate, butyl acrylate, vinyl acrylate, 2-hydroxyethyl acrylate, 4-hydroxybutyl acrylate, crotonic acid, methyl crotonate, ethyl crotonate, 3-methylcrotonic acid, methyl 3-methylcrotonate, and ethyl 3-methylcrotonate.

Examples of preferable olefins include methacrylic acid, methyl methacrylate, 2-hydroxyethyl methacrylate, acrylic acid, methyl acrylate, and 2-hydroxyethyl acrylate, and examples of more preferable olefins include methyl methacrylate and methyl acrylate.

Further examples of the olefin having a functional group used in the Diels Alder reaction include acrylonitrile, methacrylonitrile, acrolein, and methacrolein. When these olefins are used as raw materials, the monoolefin represented by general formula (4') can be produced via, for example, the routes shown in the following formula (II) and formula (III).

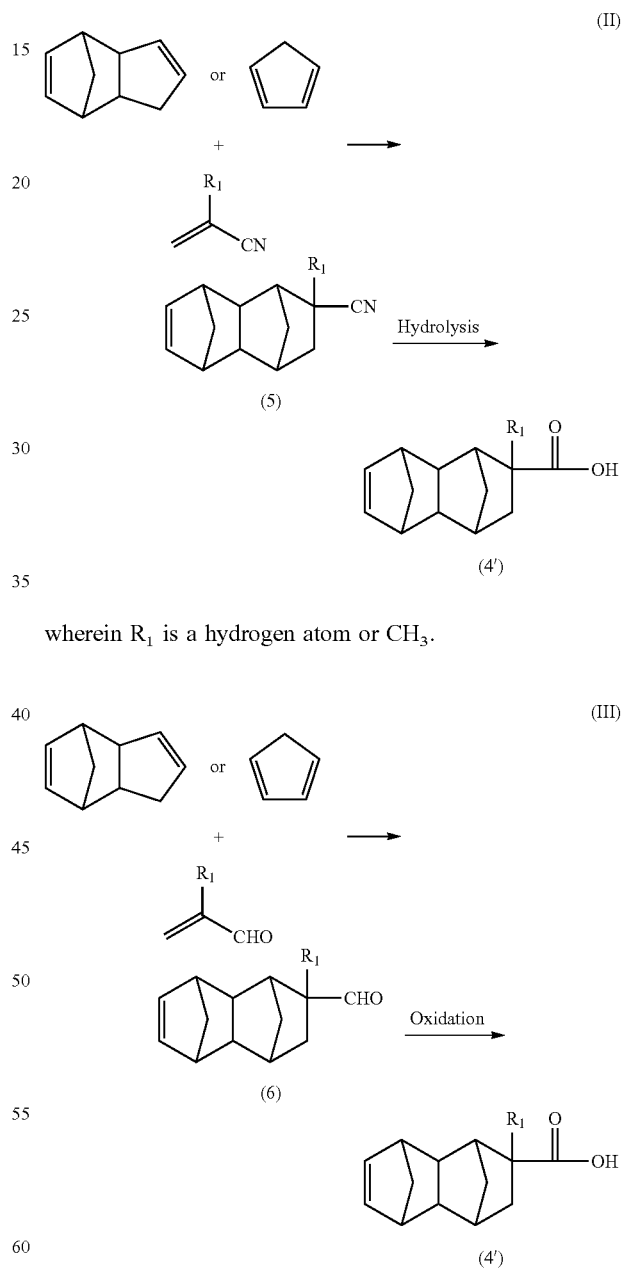

wherein $R_1$ is a hydrogen atom or $CH_3$.

Dicyclopentadiene used for the Diels Alder reaction preferably has a high purity, and the content of butadiene, isoprene, and the like is preferably reduced. The purity of dicyclopentadiene is preferably 90% or higher, and more preferably 95% or higher. Dicyclopentadiene tends to depolymerize under heating conditions and become cyclopentadiene (so-called monocyclopentadiene), and therefore it is also possible to use cyclopentadiene in place of dicyclopentadiene. It is considered that the monoolefin having 13 to 21 carbon atoms represented by general formula (4) is substantially produced via a monoolefin having 8 to 16 carbon atoms represented by the following general formula (7) (a product of a first-stage Diels Alder reaction), and it is considered that the produced monoolefin of general formula (7) undergoes a Diels Alder reaction (a second-stage Diels Alder reaction) with cyclopentadiene (Diene) present in the reaction system as a new parent diene compound (Dienophile) to produce the monoolefin having 13 to 21 carbon atoms represented by general formula (4):

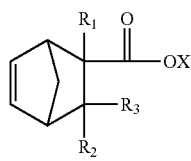

(7)

In formula (7), $R_1$ represents a hydrogen atom, $CH_3$, or $C_2H_5$; $R_2$ and $R_3$ each independently represent a hydrogen atom or $CH_3$; and X represents a hydrogen atom or a hydrocarbon group which has not more than 4 carbon atoms and which optionally comprises a hydroxyl group.

In order to allow the second-stage Diels Alder reaction to efficiently proceed, it is important that cyclopentadiene be present in the reaction system, and therefore the reaction temperature is preferably 100° C. or higher, more preferably 120° C. or higher, and even more preferably 130° C. or higher. On the other hand, in order to suppress the generation of high-boiling substances, it is preferable to carry out the reaction at a temperature of 250° C. or lower. It is also possible to use hydrocarbons, alcohols, esters, and the like as reaction solvents, and aliphatic hydrocarbons having 6 or more carbon atoms, cyclohexane, toluene, xylene, ethylbenzene, mesitylene, propanol, butanol, and the like are preferable. A known catalyst such as $AlCl_3$ may be added as necessary.

As a reaction mode of the Diels Alder reaction, various reaction modes can be adopted, such as a batch mode by a tank reactor or the like, a semi-batch mode where a substrate or a substrate solution is supplied to a tank reactor under reaction conditions, and a continuous-flow mode where a substrate or the like is allowed to flow through a tubular reactor under reaction conditions.

The reaction product obtained in the Diels Alder reaction can also be used as-is as a raw material for the next hydroformylation reaction, and it may also be subjected to the next step after purification by distillation, extraction, crystallization, or a like method.

[Production of Bifunctional Compound Having 14 to 22 Carbon Atoms Represented by (3) in Formula (I)]

The bifunctional compound having 14 to 22 carbon atoms represented by general formula (3) in the above formula (I) can be produced by, for example, subjecting the monoolefin having 13 to 21 carbon atoms represented by general formula (4), carbon monoxide, and hydrogen gas to a hydroformylation reaction in the presence of a rhodium compound and an organophosphorus compound.

The rhodium compound used in the hydroformylation reaction may be a compound that forms a complex with an organophosphorus compound and shows hydroformylating activity in the presence of carbon monoxide and hydrogen, and the form of the precursor thereof is not particularly limited. For example, a catalyst precursor substance such as rhodium acetylacetonatodicarbonyl (hereinafter referred to as $Rh(acac)(CO)_2$), $Rh_2O_3$, $Rh_4(CO)_{12}$, $Rh_6(CO)_{16}$, or $Rh(NO_3)_3$ may be introduced into a reaction mixture together with an organophosphorus compound to form a rhodium metal hydride carbonyl phosphorus complex having catalytic activity in a reaction vessel, or a rhodium metal hydride carbonyl phosphorus complex may be prepared in advance and introduced into a reactor. A preferable specific example is a method in which $Rh(acac)(CO)_2$ is reacted with an organophosphorus compound in the presence of a solvent and then introduced into a reactor together with an excess of the organophosphorus compound to form a rhodium-organophosphorus complex having catalytic activity.

What was surprising to the present inventors was that the product of the two-stage Diels Alder reaction containing an internal olefin having a relatively large molecular weight as represented by general formula (4) was hydroformylated with an extremely small amount of a rhodium catalyst. The amount of the rhodium compound used in the present hydroformylation reaction is preferably 0.1 to 60 micromoles, more preferably 0.1 to 30 micromoles, even more preferably 0.2 to 20 micromoles, and particularly preferably 0.5 to 10 micromoles per mol of the monoolefin having 13 to 21 carbon atoms represented by general formula (4), which is the substrate of the hydroformylation reaction. An amount of the rhodium compound used of less than 60 micromoles per mol of the monoolefin having 13 to 21 carbon atoms can be evaluated as being at a level where practically a recovery/recycle facility for the rhodium complex does not need to be provided. Thus, according to the present embodiment, the economic burden concerning a recovery/recycle facility can be reduced, and the cost of the rhodium catalyst can be reduced.

In the hydroformylation reaction in the present embodiment, the organophosphorus compound that forms a catalyst for the hydroformylation reaction together with the rhodium compound is not particularly limited, and examples include phosphines represented by general formula $P(-R_a)(-R_b)(-R_c)$ or phosphites represented by $P(-OR_a)(-OR_b)(-OR_c)$. Specific examples of $R_a$, $R_b$, and $R_c$ include, but are not limited to, aryl groups that may be substituted with an alkyl group or an alkoxy group having 1 to 4 carbon atoms and alicyclic alkyl groups that may be substituted with an alkyl group or an alkoxy group having 1 to 4 carbon atoms, and triphenylphosphine and triphenylphosphite are suitably used. The amount of the organophosphorus compound used is preferably 300 mol to 10000 mol, more preferably 500 mol to 10000 mol, even more preferably 700 mol to 5000 mol, and particularly preferably 900 mol to 2000 mol per mol of the rhodium atoms in the rhodium compound. When the amount of the organophosphorus compound used is 300 mol or more per mol of the rhodium atoms, there is a tendency that the stability of the rhodium metal hydride carbonyl phosphorus complex, which is the catalyst active material, can be sufficiently ensured, and, as a result, good reactivity tends to be ensured. An amount of the organophosphorus compound used of 10000 mol or less per mol of the rhodium atoms is preferable from the viewpoint of sufficiently reducing the cost of the organophosphorus compound.

Although the hydroformylation reaction can also be carried out without using a solvent, the use of a solvent that is inert to the reaction makes it possible to more suitably carry out the reaction. The solvent usable in the hydroformylation reaction is not particularly limited as long as it dissolves monoolefin having 13 to 21 carbon atoms represented by general formula (4), dicyclopentadiene or cyclopentadiene, the above rhodium compound, and the above organophosphorus compound. Specific examples thereof include, but are not limited to, hydrocarbons such as aliphatic hydrocarbons, alicyclic hydrocarbons, and aromatic hydrocarbons; esters such as aliphatic esters, alicyclic esters, and aromatic esters; alcohols such as aliphatic alcohols and alicyclic alcohols; and aromatic halides and such solvents. Among these, hydrocarbons are suitably used, and, in particular, alicyclic hydrocarbons and aromatic hydrocarbons are more suitably used.

The temperature when carrying out the hydroformylation reaction is preferably 40° C. to 160° C., and more preferably 80° C. to 140° C. When the reaction temperature is 40° C. or higher, a sufficient reaction rate tends to be obtained, and remainders of the raw-material monoolefin tend to be more suppressed. When the reaction temperature is 160° C. or lower, there is a tendency that the generation of byproducts derived from the raw-material monoolefin and the reaction product is suppressed, and deterioration of reaction results can be effectively prevented.

When the hydroformylation reaction in the present embodiment is carried out, the reaction is preferably carried out under an increased pressure of carbon monoxide (hereinafter also referred to as "CO") and hydrogen (hereinafter also referred to as "$H_2$") gas. At that time, CO and $H_2$ gas can be each independently introduced into the reaction system and, also, can be introduced into the reaction system as a mixed gas prepared in advance. The molar ratio (=CO/$H_2$) of CO and $H_2$ gas introduced into the reaction system is preferably 0.2 to 5, more preferably 0.5 to 2, and even more preferably 0.8 to 1.2. When the molar ratio of CO and $H_2$ gas is adjusted to the above range, the reaction activity of the hydroformylation reaction and selectivity for the intended aldehyde tend to be good. CO and $H_2$ gas introduced into the reaction system decreases as the reaction progresses, and therefore the reaction may be easily controlled by the use of a mixed gas of CO and $H_2$ prepared in advance.

The reaction pressure of the hydroformylation reaction is preferably 1 to 12 MPa, more preferably 1.2 to 9 MPa, and even more preferably 1.5 to 5 MPa. With the reaction pressure being 1 MPa or higher, a sufficient reaction rate tends be obtained, and there is a tendency that remainders of the raw-material monoolefin can be sufficiently suppressed. A reaction pressure of 12 MPa or lower makes an expensive facility having excellent pressure resistance unnecessary and is therefore economically advantageous. In particular, when the reaction is carried out in a batch or semi-batch mode, CO and $H_2$ gas need to be discharged or pressure-released after the end of the reaction, and a lower pressure results, in a smaller loss of CO and $H_2$ gas and is therefore economically advantageous.

As a reaction mode when carrying out the hydroformylation reaction, a batch reaction and a semi-batch reaction are suitable. A semi-batch reaction can be carried out by adding a rhodium compound, an organophosphorus compound, and the above solvent to a reactor, setting the described reaction conditions by increasing the pressure by CO/$H_2$ gas, raising the temperature, or the like, and then supplying the raw-material monoolefin or a solution thereof to the reactor.

The reaction product obtained in the hydroformylation reaction can also be used as-is as a raw material for the next reduction reaction, and it may also be subjected to the next step after purification by, for example, distillation, extraction, or crystallization.

[Production of Compound Having 14 to 22 Carbon Atoms Represented by Formula (2)]

The compound having 14 to 22 carbon atoms represented by general formula (2) in the above formula (I) can be produced by reducing the compound having 14 to 22 carbon atoms represented by general formula (3) in the presence of a catalyst having hydrogenation capability and hydrogen.

In the reduction reaction, it is preferable to use a catalyst containing at least one element selected from the group consisting of copper, chromium, iron, zinc, aluminum, nickel, cobalt, and palladium as the catalyst having hydrogenation capability. More preferable catalysts are a Cu—Cr catalyst, a Cu—Zn catalyst, a Cu—Zn—Al catalyst, a Raney-Ni catalyst, a Raney-Co catalyst, and the like, and even more preferable catalysts are a Cu—Cr catalyst and a Raney-Co catalyst.

The amount of the hydrogenation catalyst used is 1 to 100 mass %, preferably 2 to 50 mass %, and more preferably 5 to 30 mass % relative to the substrate compound having 14 to 22 carbon atoms represented by general formula (3). With the amount of the catalyst used being within these ranges, the hydrogenation reaction can be suitably carried out. When the amount of the catalyst used is 1 mass % or more, the reaction sufficiently progresses, and, as a result, there is a tendency that a sufficient yield of the intended product can be ensured. When the amount of the catalyst used is 100 mass % or less; the balance between the amount of the catalyst subjected to the reaction and the effect of improving the reaction rate tends to be good.

The reaction temperature of the reduction reaction is preferably 60 to 200° C., and more preferably 80° C. to 150° C. With the reaction temperature being 200° C. or lower, side reactions and degradation reactions are suppressed, and the intended product tends to be obtained in high yield. With the reaction temperature being 60° C. or higher, the reaction can be completed in an appropriate time, and there is a tendency that a decrease in productivity and a decrease in the yield of the intended product can be avoided.

The reaction pressure of the reduction reaction is preferably 0.5 to 10 MPa and more preferably 1 to 5 MPa as hydrogen partial pressure. With the hydrogen partial pressure being 10 MPa or lower, side reactions and degradation reactions are suppressed, and the intended product tends to be obtained in high yield. With the hydrogen partial pressure being 0.5 MPa or higher, the reaction can be completed in an appropriate time, and there is a tendency that a decrease in productivity and a decrease in the yield of the intended product can be avoided. It is also possible to allow a gas that is inert to the reduction reaction (such as nitrogen or argon) to be concomitantly present.

In the reduction reaction, a solvent can be used. Examples of the solvent used in the reduction reaction include aliphatic hydrocarbons, alicyclic hydrocarbons, aromatic hydrocarbons, and alcohols, and, in particular, alicyclic hydrocarbons, aromatic hydrocarbons, and alcohols are preferable. Specific examples include cyclohexane, toluene, xylene, methanol, ethanol, and 1-propanol.

As a reaction mode of the reduction reaction, various reaction modes can be adopted, such as a batch mode by a tank reactor or the like, a semi-batch mode where a substrate or a substrate solution is supplied to a tank reactor under reaction conditions, and a continuous-flow mode where a substrate or a substrate solution is allowed to flow through a tubular reactor filled with a shaped catalyst under reaction conditions.

The reaction product obtained in the reduction reaction can be purified by, for example, distillation, extraction, or crystallization.

(C) Method for Producing Polyester Resin

The method for polymerizing a compound represented by general formula (2) into a polyester having a constitutional unit represented by general formula (1) in the present embodiment is not particularly limited, and a conventionally known polyester production method is applicable. Examples include melt polymerization methods such as an ester exchange method and a direct esterification method, or solution polymerization methods.

When producing the polyester resin of the present embodiment, an ester interchange catalyst, an esterification catalyst, a polycondensation catalyst, or the like that is used when producing an ordinary polyester resin can be used. These catalysts are not particularly limited, and examples thereof include compounds of metals such as zinc, lead, cerium, cadmium, manganese, cobalt, lithium, sodium, potassium, calcium, nickel, magnesium, vanadium, aluminum, titanium, antimony, germanium, and tin (for example, fatty acid salts, carbonic acid salts, phosphoric acid salts, hydroxides, chlorides, oxides, and alkoxides), and magnesium metal. These can be used singly or as a combination of two or more. Among the aforementioned catalysts, compounds of manganese, cobalt, zinc, titanium, calcium, antimony, germanium, and tin are preferable, and compounds of manganese, titanium, antimony, germanium, and tin are more preferable. The amount of these catalysts used is not particularly limited, and the amount in terms of metal component relative to the raw materials of the polyester resin is preferably 1 to 1000 ppm, more preferably 3 to 750 ppm, and even more preferably 5 to 500 ppm.

The reaction temperature in the polymerization reaction depends on the kind of the catalyst, the amount of the catalyst used, and the like. It is usually selected from the range of 150° C. to 300° C., and is preferably 180° C. to 280° C. in consideration of the reaction rate and the coloration of the resin. It is preferable to regulate the pressure in the reaction layer eventually to 1 kPa or lower and, more preferably, eventually to 0.5 kPa or lower, from atmospheric pressure.

When performing the polymerization reaction, a phosphorus compound may be added as desired. Examples of the phosphorus compound include, but are not limited to, phosphoric acid, phosphorous acid, phosphoric acid esters, and phosphorous acid esters. Examples of phosphoric acid esters include, but are not limited to, methyl phosphate, ethyl phosphate, butyl phosphate, phenyl phosphate, dimethyl phosphate, diethyl phosphate, dibutyl phosphate, diphenyl phosphate, trimethyl phosphate, triethyl phosphate, tributyl phosphate, and triphenyl phosphate. Examples of phosphorous acid esters include, but are not limited to, methyl phosphite, ethyl phosphite, butyl phosphite, phenyl phosphite, dimethyl phosphite, diethyl phosphite, dibutyl phosphite, diphenyl phosphite, trimethyl phosphite, triethyl phosphite, tributyl phosphite, and triphenyl phosphite. These can be used singly or as a combination of two or more. The concentration of phosphorus atom in the polyester resin of the present embodiment is preferably 1 to 500 ppm, more preferably 5 to 400 ppm, and even more preferably 10 to 200 ppm.

As described above, the polyester resin of the present embodiment may contain a further constitutional unit other than constitutional unit (1) as long as the performance is not impaired. The further constitutional unit is suitably selected from a constitutional unit derived from a dicarboxylic acid and/or a derivative thereof, a diol constitutional unit, a unit derived from a monoalcohol, a unit derived from a polyalcohol having a valency of 3 or greater, a unit derived from a monocarboxylic acid, a unit derived from a polycarboxylic acid, and a unit derived from an oxyacid other than the compound represented by general formula (2), and can be polymerized together with the compound represented by general formula (2) by applying a conventionally known polyester production method. Examples of the conventionally known polyester production method include, but are not limited to, melt polymerization methods such as an ester exchange method and a direct esterification method, or solution polymerization methods.

When producing the polyester resin of the present embodiment, various stabilizers such as etherification inhibitors, heat stabilizers, and light stabilizers, polymerization regulators, and the like can be used.

Various additives and molding aids can be added to the polyester resin of the present embodiment as long as the object of the present embodiment is not impaired, such as antioxidants, light stabilizers, UV absorbers, plasticizers, extenders, delustrants, drying regulators, antistatic agents, antisettling agents, surfactants, flowability improvers, drying oils, waxes, fillers, colorants, reinforcing agents, surface smoothing agents, leveling agents, curing reaction promoters, and thickeners.

EXAMPLES

Below, the present invention will now be described in further detail below by way of Examples, but the scope of the invention is not limited to these Examples. Methods for evaluating polyester resins were as follows.

(1) Weight Average Molecular Weight (Mw)

The polyester resin was dissolved in tetrahydrofuran to have a polyester resin concentration of 0.2 mass % and measured by gel permeation chromatography (GPC) to determine the molecular weight in reference to standard polystyrene. A column TSKgel SuperHM-M manufactured by Tosoh Corporation was used for GPC measurement at a column temperature of 40° C. The eluent tetrahydrofuran was allowed to flow at a flow rate of 0.6 mL/min for measurement by an RI detector.

(2) Glass Transition Temperature (Tg)

The glass transition temperature of the polyester resin was measured as follows. Using a differential scanning calorimeter (manufactured by Shimadzu Corporation, trade name: DSC/TA-60WS), about 10 mg of the polyester resin was placed in an unsealed aluminum container and heated to 280° C. at a heating rate of 20° C./min in a nitrogen gas stream (30 mL/min), and the dissolved polyester resin was rapidly cooled to give a measurement sample. The sample was measured under the same conditions, and the temperature which changes by only ½ of the difference in the baseline between the DSC curve before and that after transition was regarded as the glass transition temperature.

(3) Transparency

A sample was formed by pressing the polyester resin into a disk (thickness 3 mm) to measure the total light transmission rate. A color-difference/turbidity meter (manufactured by Nippon Denshoku Industries Co., Ltd., trade name: COH-400) was used for measurement.

(4) Water Vapor Transmission Coefficient (g·Mm/m²·Day)

A water vapor transmission rate testing system (manufactured by MOCON Inc., trade name: PERMATRAN-W Model 1/50G) was used to measure the water vapor transmission rate of a coated substrate under conditions having 40° C. and a relative humidity of 90%, and the water vapor transmission coefficient of the coating film was calculated using the following equation:

$$1/R_1 = 1/R_2 + DFT/P$$

where
$R_1$=Water vapor transmission rate of coated substrate (g/m²·day)
$R_2$=Water vapor transmission rate of substrate (g/m²·day)
DFT=Thickness of coating film (mm)
P=Water vapor transmission coefficient of coating film (g·mm/m²·day)

(5) Photoelastic Coefficient (m²/N)

The photoelastic coefficient was calculated using an ellipsometer (manufactured by Jasco Corporation, M220) from measurement of birefringence relative to load change at, a wavelength of 633 nm using an optical film prepared by solution casting method.

Monomer Synthesis Example 173 g (2.01 mol) of methyl acrylate and 167 g (1.26 mol) of dicyclopentadiene were charged into a 500 mL stainless-steel reactor and reacted at 195° C. for 2 hours. From the reaction, a reaction solution containing 96 g of monoolefin represented by the following formula (4a) was obtained, this was purified by distillation, and then some was subjected to the following reaction.

Using a 300 mL stainless-steel reactor, the hydroformylation reaction of the monoolefin represented by formula (4a) that had been purified by distillation was carried out with CO/H₂ mixed gas (CO/H₂ molar ratio=1). To the reactor were added 70 g of the monoolefin represented by formula (4a), 140 g of toluene, 0.50 g of triphenylphosphite, 550 μL of a separately prepared toluene solution of Rh(acac) (CO), (concentration 0.003 mol/L). Replacement by nitrogen and CO/H₂ mixed gas was each performed 3 times, then the pressure inside the system was increased by CO/H₂ mixed gas, and a reaction was carried out at 100° C. at 2 MPa for 5 hours. After the end of the reaction, a gas chromatography analysis of the reaction solution verified that the reaction solution (degree of conversion 98%, selectivity 97%) contained 76 g a compound represented by formula (3a) and 1.4 g of monoolefin represented by formula (4a), also, this was purified by distillation, and some was subjected to the following reaction.

To a 300 mL stainless-steel reactor were added 54 g of the compound represented by formula (3a) that had been purified by distillation, 7 mL of a sponge cobalt catalyst (manufactured by Nikko Rica Corporation: R-400), and 109 g of toluene, the system was pressurized by hydrogen gas, and a reaction was carried out at 3 MPa at 100° C. for 9 hours. After the reaction, the catalyst was filtered off from the resulting slurry through a membrane filter having a pore size of 0.2 μm. Thereafter, an evaporator was used to distill off the solvent, and gas chromatography and GC-MS analyses verified that 51 g of a main product having a molecular weight of 250 represented by formula (2a) was contained (main-product yield 93%). This was further purified by distillation, and the main product was obtained.

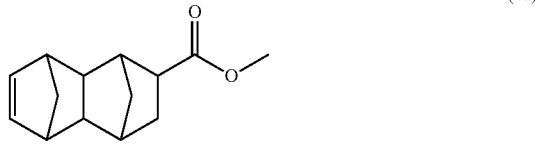

(4a)

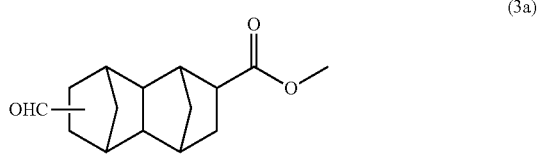

(3a)

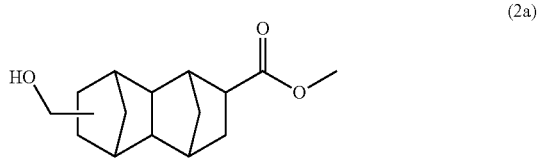

(2a)

<Identification of Product>

Figure 2:
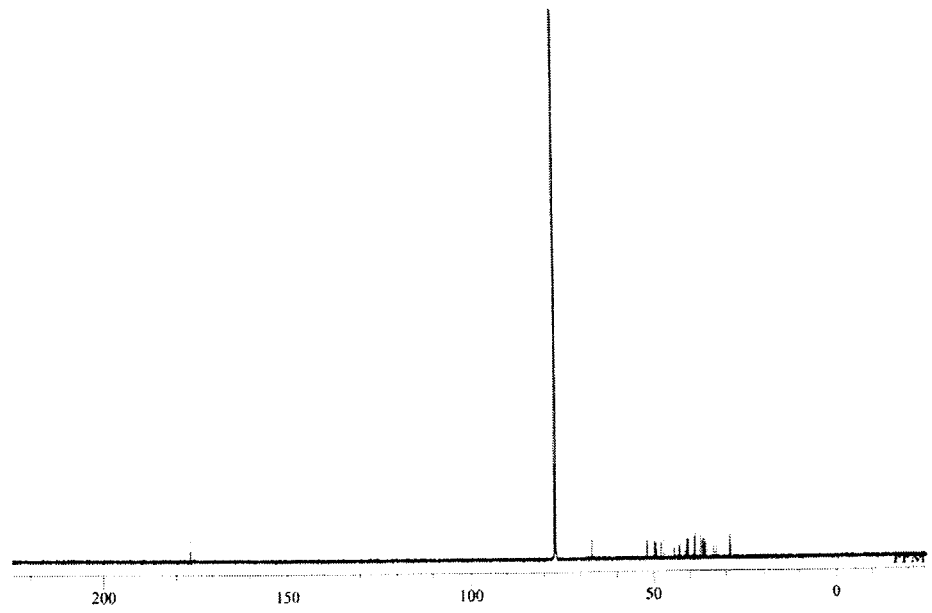
FIG. 2 shows the results of 13C-NMR measurement of the main reaction product obtained in the monomer synthesis example.
Figure 3:
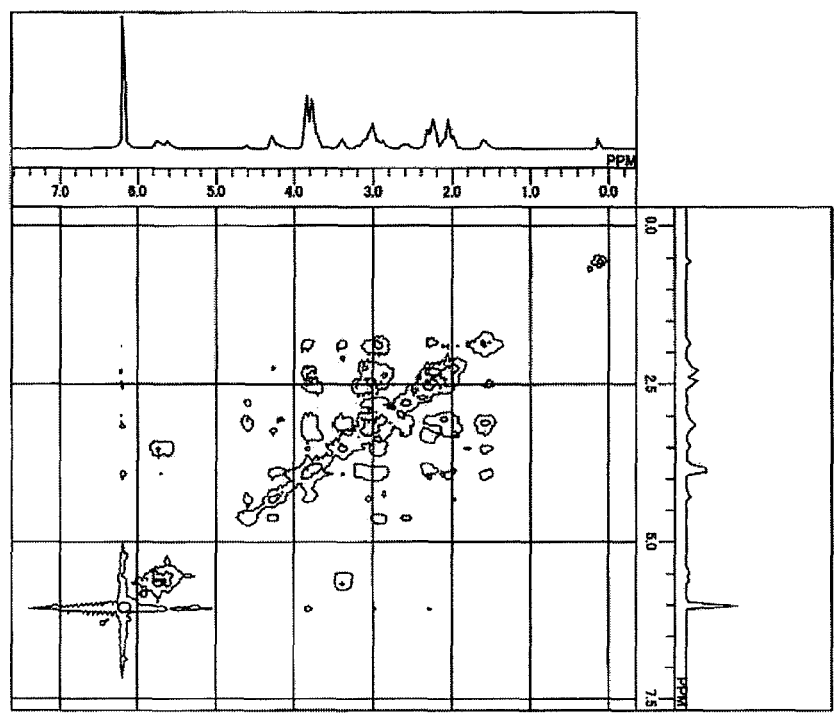
FIG. 3 shows the results of COSY-NMR measurement of the main reaction product obtained in the monomer synthesis example.

The components obtained in the monomer synthesis example were analyzed by NMR. NMR spectra were shown in FIGS. 1 to 3. From the results of a GC-MS analysis shown below and NMR analyses of FIGS. 1 to 3, the main product obtained in the monomer synthesis example was verified as a compound represented by the above formula (2a).

<Analytical Methods>

1) Gas Chromatography Measurement Conditions
    Analyzer: Capillary Gas Chromatograph GC-2010 Plus manufactured by Shimadzu Corporation
    Analytical column: InertCap 1 manufactured by GL Sciences Inc. (30 m, 0.32 mm I.D., film thickness 0.25 μm
    Oven temperature: 60° C. (for 0.5 min)—15° C./min—280° C. (for 4 min)
    Detector: FID, temperature 280° C.

2) GC-MS Measurement Conditions
    Analyzer: GCMS-QP2010 Plus manufactured by Shimadzu Corporation
    Ionization voltage: 70 eV
    Analytical column: DB-1 manufactured by Agilent Technologies (30 m, 0.32 mm I.D., film thickness 1.00 μm)
    Oven temperature: 60° C. (for 0.5 min)—15° C./min—280° C. (for 4 min)

3) NMR Measurement Conditions
    Apparatus: JNM-ECA500 (500 MHz) manufactured by JEOL Ltd.
    Measurement mode: 1H-NMR, 13C-NMR, COSY-NMR
    Solvent: CDCl₃ (heavy chloroform)
    Internal standard: tetramethylsilane Example 1

45 g of the compound represented by formula (2a) obtained in the monomer synthesis example and 0.007 g of tetrabutyl titanate were charged into a 200 mL polyester production apparatus equipped with a partial condenser, a total condenser, a cold trap, a stirrer, a heater, and a nitrogen inlet tube, heated to 230° C. in a nitrogen atmosphere, and then retained for 1 hour. Thereafter, heating and depressurization were gradually carried out, and eventually polycondensation was carried out at 270° C. at 0.1 kPa or lower. The reaction was terminated when an appropriate melt viscosity was reached, and a polyester resin was thus obtained. The resulting polyester resin had a weight average molecular weight of 26000, a glass transition temperature of 167° C., and a total light transmission rate of 91%.

Example 2

11.5 g of the compound represented by formula (2a) obtained in a monomer synthesis example and 0.005 g of tetrabutyl titanate were charged into a 30 mL polyester production apparatus equipped with a partial condenser, a total condenser, a cold trap, a stirrer, a heater, and a nitrogen inlet tube, heated to 230° C. in a nitrogen atmosphere, and then retained for 1 hour. Thereafter, heating and depressurization were gradually carried out, and eventually polycondensation was carried out at 270° C. at 0.1 kPa or lower. The reaction was terminated when an appropriate melt viscosity was reached, and a polyester resin was thus obtained. The resulting polyester resin had a weight average molecular weight of 46800, a glass transition temperature of 171° C., and a total light transmission rate of 91%.

Then, 20 parts by mass of the resulting polyester resin and 80 parts by mass of tetrahydrofuran were mixed to obtain an application liquid having a solid content concentration of 20 mass %. A stretched polyethylene terephthalate film (Ester Film E5100 manufactured by Toyobo Co., Ltd.) having a thickness of 50 μm was used as a substrate, a bar coater No. 20 was used to apply the application liquid to the substrate, and the application liquid was dried at 100° C. for 60 minutes to obtain a coat film. The water vapor transmission rate of the resulting coat film was evaluated. The thickness of the coat layer was 5.7 μm, and the water vapor transmission coefficient calculated from the water vapor transmission rate was 1.14 g·mm/m²·day (40° C. 90% RH).

Using the polyester resin obtained above, an optical film was prepared by the solution casting method described below. That is, the polyester resin was dissolved to a concentration of 5 wt % in dichloromethane and solution-cast onto a cast plate that had been verified as being level, the solvent was volatilized while regulating the amount of the solvent being evaporated from the cast solution, and a transparent optical film having a thickness of 50 μm was thus obtained. The resulting optical film was sufficiently dried at a temperature no higher than the glass transition temperature using a dryer, a sample having 5 cm×1 cm was cut out, and the photoelastic coefficient evaluated using an ellipsometer was −0.4×10⁻¹² (m²/N).

Comparative Monomer Synthesis Example 95 g (1.10 mol) of methyl acrylate and 105 g (0.79 mol) of dicyclopentadiene were charged into a 500 mL stainless-steel reactor and reacted at 195° C. for 2 hours. A reaction solution containing 127 g of monoolefin represented by the following formula (8) and 55 g of monoolefin represented by formula (2a) was obtained. This was purified by distillation to thereby obtain monoolefin represented by formula (8), and some was subjected to the following reaction.

Using a 500 mL stainless-steel reactor, the hydroformylation reaction of the monoolefin represented by formula (8) that had been purified by distillation was carried out with CO/H₂ mixed gas (CO/H₂ molar ratio=1). To the reactor were added 100 g of the monoolefin represented by formula (8), 200 g of toluene, 0.614 g of triphenylphosphite, 200 μL of a separately prepared toluene solution of Rh(acac) (CO)₂ (concentration 0.0097 mol/L). Replacement by nitrogen and CO/H: mixed gas was each performed 3 times, then the pressure inside the system was increased by CO/H₂ mixed gas, and a reaction was carried out at 100° C. at 2 MPa for 4.5 hours. After the end of the reaction, a gas chromatography analysis of the reaction solution verified that the reaction solution (degree of conversion 100%, selectivity 94%) contained 113 g a bifunctional compound represented by formula (9), also, this was purified by distillation, and some was subjected to the following reaction.

To a 500 mL stainless-steel reactor were added 70 g of the bifunctional compound represented by formula (9) that had been purified by distillation, 14 mL of a sponge cobalt catalyst (manufactured by Nikko Rica Corporation: R-400), and 210 g of toluene, the system was pressurized by hydrogen gas, and a reaction was carried out at 3 MPa at 100° C. for 3.5 hours. After the reaction, the resulting slurry was filtered through a membrane filter having a pore size of 0.2 μm to filter the catalyst. Thereafter, an evaporator was used to distill off the solvent, and a GC-MS analysis verified that 69 g of a main product having a molecular weight of 184 was contained (main-product yield 98%). This was further purified by distillation, and the main product (10) was obtained.

(8)

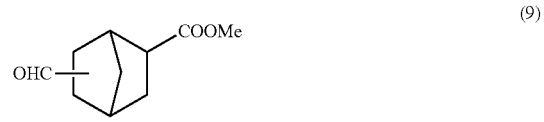

(9)

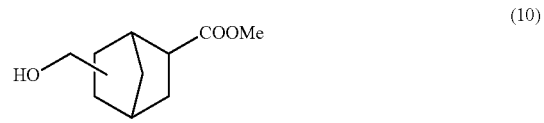

(10)

Comparative Example 1

A reaction was carried out by the same method as in Example 2 to obtain a polyester resin except that the compound represented by formula (10) obtained in the comparative monomer synthesis example was used as a raw-material monomer, and the final temperature of polycondensation was 265° C. Further, the resulting resin was used to form a coat film by the same procedure as in Example 2, the water vapor transmission rate was measured, and the water vapor transmission coefficient was calculated. The weight average molecular weight, the glass transition temperature, and the water vapor transmission coefficient of the resulting resin are shown in Table 1. The total light transmission rate of the resulting polyester resin was 91%.

TABLE 1

|  |  | Example 2 | Comparative Example 1 | Substrate alone |
|---|---|---|---|---|
| Resin evaluation |  |  |  |  |
| Mw |  | 46800 | 35000 | — |
| Mn |  | 17200 | 12400 | — |
| Tg | ° C. | 171 | 90 | — |

TABLE 1-continued

|  |  | Example 2 | Comparative Example 1 | Substrate alone |
|---|---|---|---|---|
| Water vapor transmission rate measurement (conditions: 40° C./90% RH) | | | | |
| Water vapor transmission rate (substrate + coat layer) | g/m2 · day | 12.9 | 13.4 | 13.8 |
| Coat layer thickness | μm | 5.7 | 6.9 | — |
| Water vapor transmission coefficient of coat layer | g · mm/m2 · day | 1.1 | 3.2 | — |

The water vapor transmission rate of Example 2 was 12.9 g/m²·day, lower than the water vapor transmission rate of 13.8 g/m²·day attained with a substrate alone. When evaluated in terms of water vapor transmission coefficient, the water vapor transmission coefficient of the resin of Example 2 was about ⅓ of the resin of Comparative Example 1.

The present application is based on a Japanese Patent Application (Japanese Patent Application No. 2015-107183) filed on May 27, 2015 and a Japanese Patent Application (Japanese Patent Application No. 2016-061737) filed on Mar. 25, 2016, and the entire contents of which are hereby incorporated by reference.

INDUSTRIAL APPLICABILITY

Having excellent transparency and heat resistance, the polyester resin of the present invention can be suitably used in, for example, materials required to have transparency and heat resistance, and accordingly the industrial significance of the present invention is considerable.

The invention claimed is:

1. A polyester resin comprising a constitutional unit represented by general formula (1):

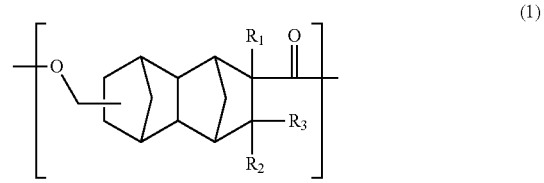

(1)

wherein $R_1$ is a hydrogen atom, $CH_3$, or $C_2H_5$; and $R_2$ and $R_3$ are each independently a hydrogen atom or $CH_3$.

2. A method for producing a polyester resin, comprising the step of polymerizing a compound represented by general formula (2):

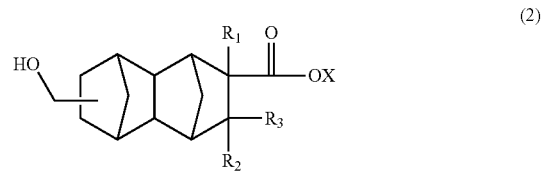

(2)

wherein $R_1$ is a hydrogen atom, $CH_3$, or $C_2H_5$; $R_2$ and $R_3$ are each independently a hydrogen atom or $CH_3$; and X is a hydrogen atom or a hydrocarbon group which has not more than 4 carbon atoms and which optionally comprises a hydroxyl group.

* * * * *